United States Patent
Wang et al.

(10) Patent No.: US 7,838,127 B1
(45) Date of Patent: *Nov. 23, 2010

(54) METAL QUINOLINE COMPLEXES

(75) Inventors: Ying Wang, Wilmington, DE (US); Norman Herron, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1287 days.

This patent is subject to a terminal disclaimer.

(21) Appl. No.: 11/305,491

(22) Filed: Dec. 15, 2005

Related U.S. Application Data

(60) Provisional application No. 60/640,392, filed on Dec. 29, 2004, provisional application No. 60/694,935, filed on Jun. 28, 2005.

(51) Int. Cl.
*H01L 51/54* (2006.01)
*C07D 401/14* (2006.01)

(52) U.S. Cl. .............. 428/690; 428/917; 313/504; 313/506; 252/301.16; 257/40; 257/E51.043; 546/7; 546/10; 546/159

(58) Field of Classification Search .......... 428/690, 428/917; 313/504, 506; 257/40, 88–90, 257/94–98, E51.043; 252/301.16–301.22, 252/301.26, 301.32, 301.33
See application file for complete search history.

(56) References Cited

U.S. PATENT DOCUMENTS

| 5,728,801 | A | 3/1998 | Wu et al. ............... 528/422 |
| 5,929,194 | A | 7/1999 | Woo et al. .............. 528/229 |
| 5,948,552 | A | 9/1999 | Antoniadis et al. ........ 428/690 |
| 6,303,238 | B1 | 10/2001 | Thompson et al. .......... 428/690 |
| 2001/0019782 | A1 | 9/2001 | Igarashi et al. ........... 428/690 |
| 2004/0197601 | A1* | 10/2004 | Thompson et al. .......... 428/690 |
| 2004/0247936 | A1* | 12/2004 | Nakashima et al. ......... 428/690 |

FOREIGN PATENT DOCUMENTS

| EP | 1 191 612 A2 | 3/2002 |
| EP | 1 191 614 A2 | 3/2002 |
| JP | 11-204260 A | * 7/1999 |
| WO | WO 00/70655 | 11/2000 |
| WO | WO 01/41512 A1 | 6/2001 |
| WO | WO 02/02714 A2 | 1/2002 |
| WO | WO 02/15645 A1 | 2/2002 |
| WO | WO 02/20459 A1 | 3/2002 |
| WO | WO 03/037836 A1 | 5/2003 |
| WO | WO 2004/018588 A1 | 3/2004 |

OTHER PUBLICATIONS

Machine translation of JP 11-204260 A (1999).*
Gustafsson, G. et al., "Flexible Light-Emitting Diodes made from Soluble Conducting Polymer", *Nature*, 1992, 357, 477-479.
O'Brien, D.F. et al., "Electrophosphoresence from a Doped Polymer Light Emitting Diode", *Synthetic Metals*, 2001, 116(1-3), 379-383.
Campbell, I.H. et al., "Excitation Transfer Processes in a phosphor-doped poly (*p*-phenylene vinylene) Light-Emitting Diode" *Physical Review B*, 65, 085210-1-085210-8.
Othmer, K., *Encyclopedia of Chemical Technology*, 1996, 18 (4$^{th}$ Ed), 837-860.

* cited by examiner

*Primary Examiner*—D. Lawrence Tarazano
*Assistant Examiner*—Michael Wilson
(74) *Attorney, Agent, or Firm*—Woodcock Washburn LLP

(57) ABSTRACT

Provided are organic electronic devices comprising at least one layer comprising at least one complex of the formula:

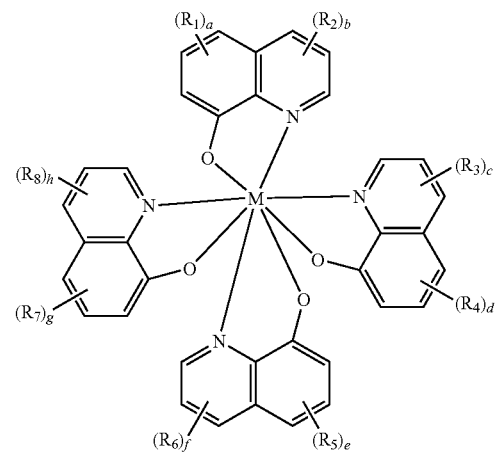

where M is Ti, Zr, Hf, Nb, Re, Sn, and Ge; $R^1$, $R^2$, $R^3$, $R^4$, $R^5$, $R^6$, $R^7$, and $R^8$ are each independently F, Cl, $CF_3$, diarylamine, carbazolyl, alkoxy, cyano, alkyl or aryl, wherein at least one of $R^1$, $R^2$, $R^3$, $R^4$, $R^5$, $R^6$, $R^7$, and $R^8$ is carbazolyl; and a, b, c, d, e, f, g, and h are each 0, 1, 2, or 3, at least one of which is other than zero.

12 Claims, 1 Drawing Sheet

METAL QUINOLINE COMPLEXES

CROSS REFERENCE TO RELATED APPLICATIONS

This application claims benefit to U.S. Application Nos. 60/640,392, filed Dec. 29, 2004 and 60/694,935, filed Jun. 28, 2005, the disclosures of which are each incorporated herein by reference in their entireties.

FIELD OF THE DISCLOSURE

This disclosure relates generally to metal quinoline complexes, for example, their use in organic electronic devices, and materials and methods for fabrication of the same.

BACKGROUND INFORMATION

Organic electronic devices convert electrical energy into radiation, detect signals through electronic processes, convert radiation into electrical energy, or include one or more organic semiconductor layers. Most organic electronic devices include a conductive layer (such as a light-emitting or photoactive layer) positioned between two electrodes.

Thus, what is needed are new materials for organic electronic devices.

SUMMARY

In one embodiment, provided are organic electronic devices comprising at least one layer comprising at least one complex of the formula:

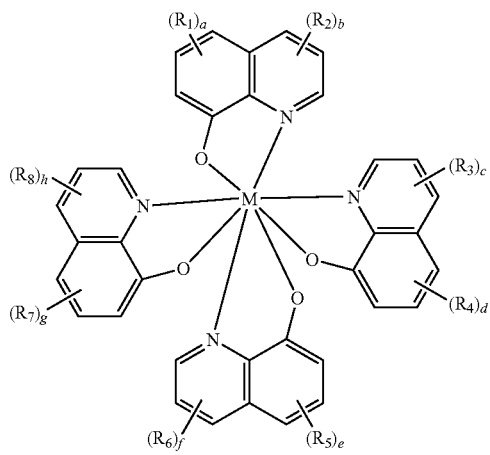

wherein:

M is selected from Ti, Zr, Hf, Nb, Re, Sn, and Ge, $R^1$, $R^2$, $R^3$, $R^4$, $R^5$, $R^6$, $R^7$, and $R^8$ are each independently F, Cl, $CF_3$, diarylamine, carbazolyl, alkoxy, cyano, alkyl or aryl; and a, b, c, d, e, f, g, and h are each 0, 1, 2, or 3;

provided that at least one of $R^1$, $R^2$, $R^3$, $R^4$, $R^5$, $R^6$, $R^7$, and $R^8$ is F, Cl, $CF_3$, diarylamine, carbazolyl, alkoxy, or cyano.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
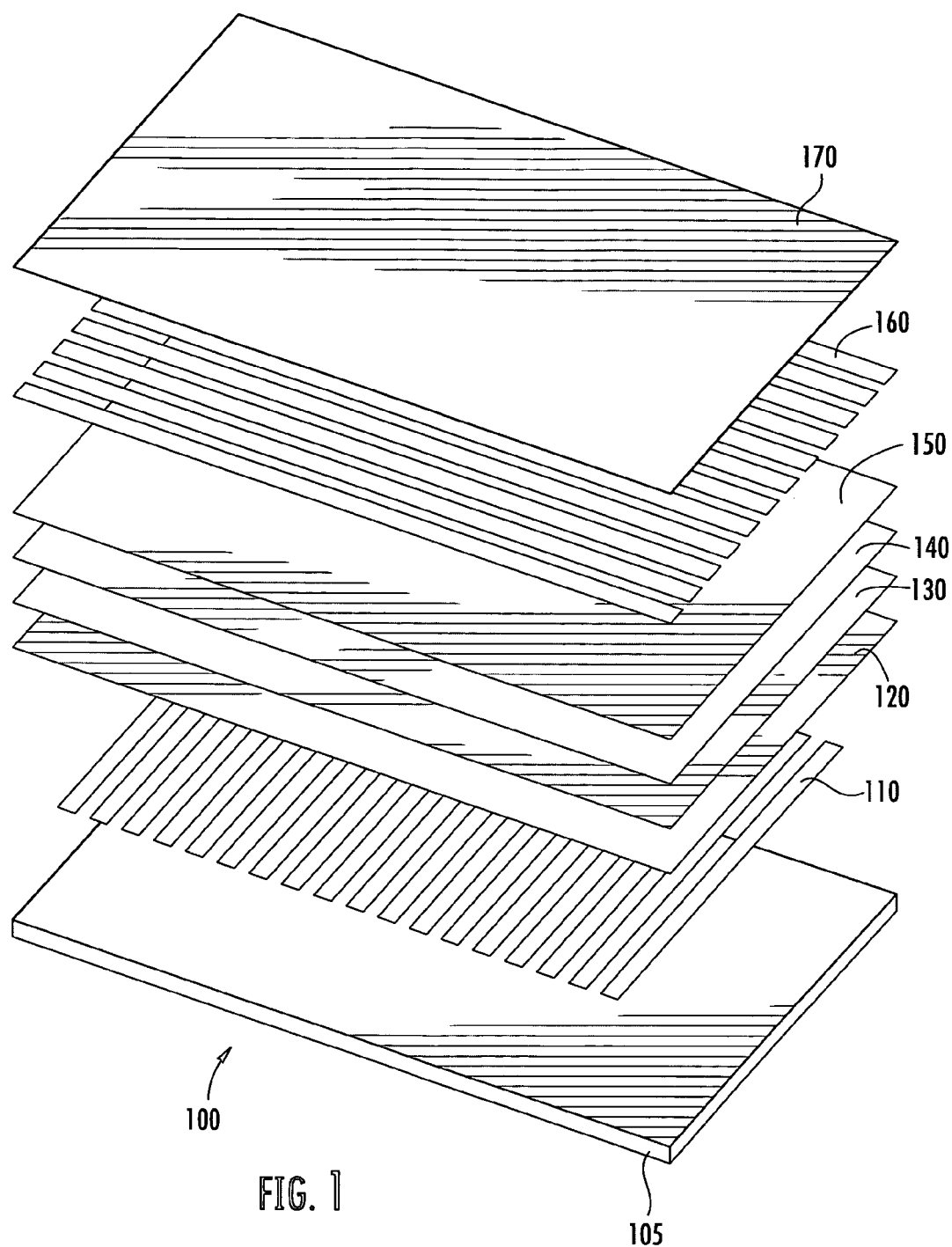
FIG. 1 includes an illustrative example of one inventive organic electronic device.

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Provided are organic electronic devices comprising at least one layer comprising at least one complex of the formula:

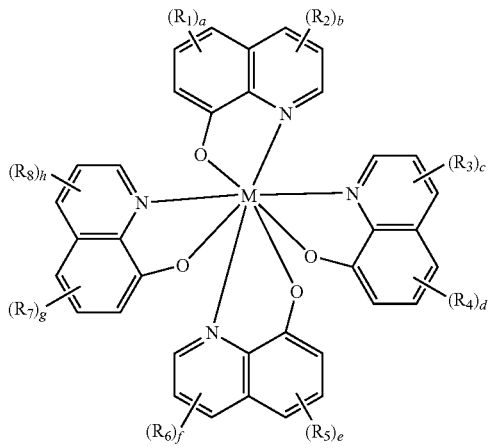

wherein:

M is selected from Ti, Zr, Hf, Nb, Re, Sn, and Ge, $R^1$, $R^2$, $R^3$, $R^4$, $R^5$, $R^6$, $R^7$, and $R^8$ are each independently F, Cl, $CF_3$, diarylamine, carbazolyl, alkoxy, cyano, alkyl or aryl; and a, b, c, d, e, f, g, and h are each 0, 1, 2, or 3;

provided that at least one of $R^1$, $R^2$, $R^3$, $R^4$, $R^5$, $R^6$, $R^7$, and $R^8$ is F, Cl, $CF_3$, diarylamine, carbazolyl, alkoxy, or cyano.

In some embodiments, the layer is a charge transport layer. In some embodiments, the device of claim 2 wherein the layer is an electron transport layer.

In some embodiments, at least one of $R^1$, $R^2$, $R^3$, $R^4$, $R^5$, $R^6$, $R^7$, and $R^8$ is diarylamine or carbazolyl. In some embodiments, at least one of $R^1$, $R^2$, $R^3$, $R^4R^5$, $R^6$, $R^7$, and $R^8$ are F or $CF_3$.

In some embodiments, M is Ti or Zr. In some embodiments, M is Zr.

In some embodiments, at least one of the $R^1$, $R^2$, $R^3$, $R^4$, $R^5$, $R^6$, $R^7$, and $R^8$ groups is diphenylamino. In some embodiments, M is Zr and a, b, c, d, e, f, g, and h are each 0 or 1.

In some embodiments, the complex is:

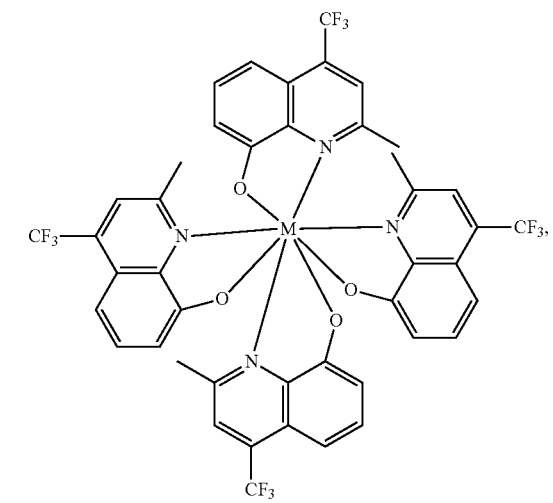

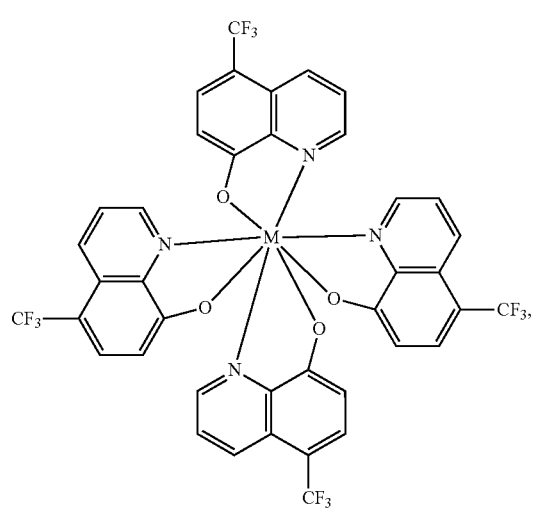

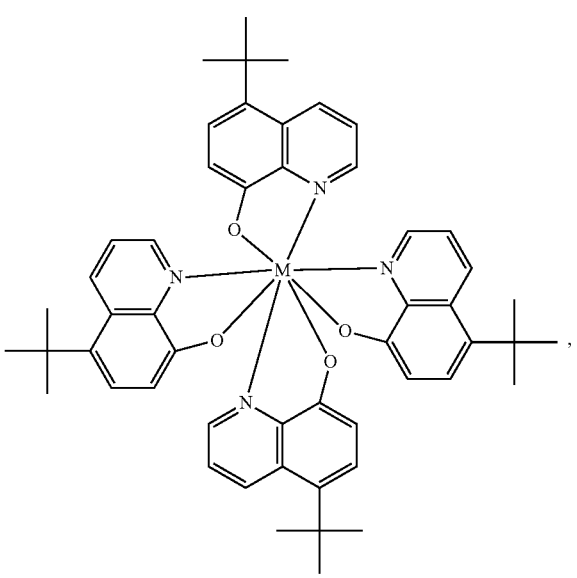

-continued

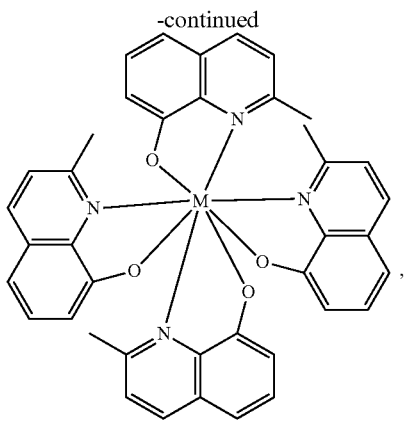

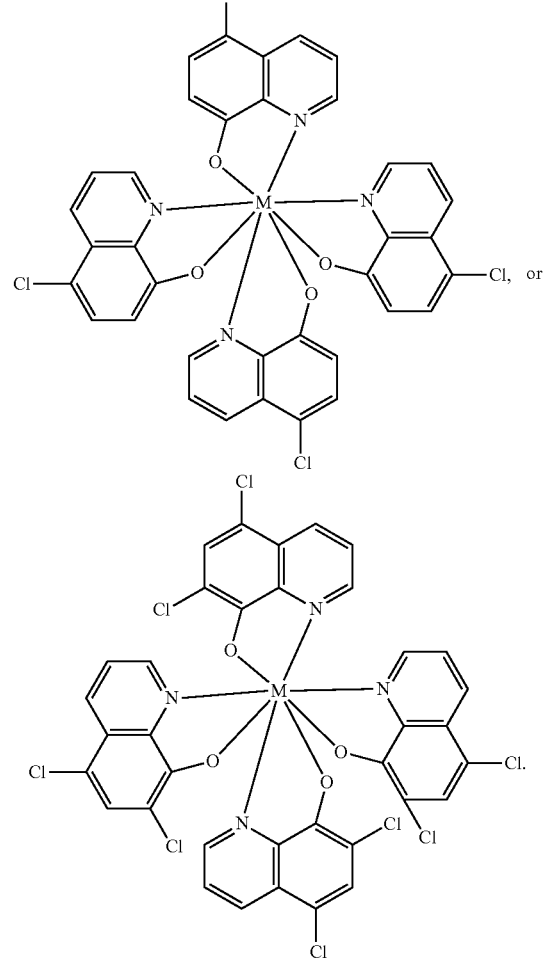

Also provided are articles useful in the manufacture of an organic electronic device comprising an electron transport layer which comprises at least one complex disclosed herein.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Illustrative Example of Electronic Devices, and finally Examples.

1. DEFINITIONS AND CLARIFICATION OF TERMS

Before addressing details of embodiments described below, some terms are defined or clarified.

As used herein, the term "alkyl" includes both branched and straight-chain saturated aliphatic hydrocarbon groups having the specified number of carbon atoms. Unless otherwise indicated, the term is also intended to include cyclic groups. Examples of alkyl groups include methyl, ethyl, propyl, isopropyl, isobutyl, secbutyl, tertbutyl, pentyl, isopentyl cyclopentyl, hexyl, cyclohexyl, isohexyl and the like. The term "alkyl" further includes both substituted and unsubstituted hydrocarbon groups. In certain embodiments alkyl groups have 1 to 12 carbon atoms. In other embodiments, the group has 1 to 6 carbon atoms.

The term "aryl" means an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 20 carbon atoms.

Unless otherwise indicated, all groups can be substituted or unsubstituted.

An optionally substituted group, such as, but not limited to, alkyl or aryl, may be substituted with one or more substituents which may be the same or different. Suitable substituents include alkyl, aryl, nitro, cyano, —$N(R^7)(R^8)$, halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, —$S(O)_2$—$N(R^7)(R^8)$, —$C(=O)$—$N(R^7)(R^8)$, $(R^7)(R^8)$N-alkyl, $(R^7)(R^8)$N-alkoxyalkyl, $(R^7)(R^8)$N-alkylaryloxyalkyl, —$S(O)_s$-aryl (where s=0-2) or —$S(O)_s$-heteroaryl (where s=0-2). Each $R^7$ and $R^8$ is independently an optionally substituted alkyl, cylcoalkyl, or aryl group. $R^7$ and $R^8$, together with the nitrogen atom to which they are bound, can form a ring system in certain embodiments. One example of a substituted alkyl group is trifluoromethyl.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector).

As used herein, The term "charge transport", when referring to a layer or material, is intended to mean that such layer or material facilitates migration of such charge through the thickness of such layer, material, member, or structure with relative efficiency and small loss of charge, and is meant to be broad enough to include materials that may act as a hole transport or an electron transport material. The term "electron transport" when referring to a layer or material means such a layer or material, member or structure that promotes or facilitates migration of electrons through such a layer or material into another layer, material, member or structure with relative efficiency and small loss of charge. "Hole transport" when referring to a layer, material, member, or structure, is intended to mean such layer, material, member, or structure facilitates migration of positive charges through the thickness of such layer, material, member, or structure with relative efficiency and small loss of charge.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The use of "a" or "an" are employed to describe elements and components of the invention. This is done merely for convenience and to give a general sense of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{St}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. ILLUSTRATIVE EXAMPLES OF ELECTRONIC DEVICES

Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer*, Nature 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 (4$^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino) phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p(diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino) styryl]-5-[p-(diethylamino)phenyl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or bandgap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

3. EXAMPLES

The concepts described herein will be further described in the following examples, which do not limit the scope of the invention described in the claims.

Example 1

Zirconium complex of
2-methyl-4-trifluoromethyl-8-hydroxyquinoline

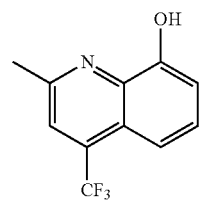

In a glove box, tetrachlorozirconium (0.233 g) was dissolved in 10 mL methanol in a 250 mL RB flask. 0.91 g 2-methyl-4-trifluoromethyl-8-hydroxyquinoline dissolved in 10 mL methanol solution was added with stirring. The mixture was stirred and heated and the yellow orange solution becomes slightly cloudy. 0.4 g triethylamine in 20 mL methanol was added slowly and the solution generated a yellow ppt. After warming to reflux for 10 mins the solution was yellow and turbid. The yellow solid was collected by filtration, washed with a little cold methanol then suction dried. Product was collected as ~0.86 g of bright yellow free-flowing microcrystals. Crystals were freely soluble in methylene chloride and toluene and may be recrystallized from methylene chloride/methanol to precipitate a bright yellow crystalline solid in ~0.7 g yield. 1-H nmr spectra were indicative of multiple isomers.

Example 2

Zirconium complex of 5-chloro-8-hydroxyquinoline

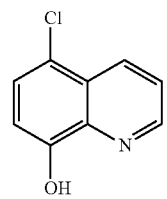

In a glove box, tetrachlorozirconium 0.23 g was dissolved into 25 mL methanol and added to 0.72 g 5-chloro-8-hydroxyquinoline (Aldrich) also dissolved in a minimum volume of methanol with stirring. The solution immediately turned orange red and became warm. 0.45 g sodium t-butoxide was added dropwise and the solution became warm with a yellow-orange ppt. This mixture was refluxed for 15 mins in the glove box. The solution remained bright orange with a dense yellow-orange ppt. The yellow solid was filtered and then dissolved into methylene chloride, filtered again and evaporated to dryness in vacuum. The recovered yellow solid was green photoluminescent. The product was modestly soluble in methylene chloride and has the 1-H nmr spectrum consistent with the desired complex wet with a little toluene.

Example 3

Zirconium complex of 5,7-dichloro-8-hydroxyquinoline

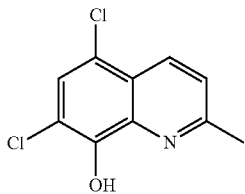

In a glove box, tetrachlorozirconium (0.23 g) was dissolved in 10 mL methanol (gets hot) and added to 0.92 g 5,7-dichloro-2-methyl-8-hydroxyquinoline (Aldrich) also dissolved in 10 mL methanol with stirring. The solution immediately turned yellow and became warm. 0.45 g sodium t-butoxide solid was slowly added and the solution became hot with a yellow ppt. This mixture was refluxed for 15 mins in the glove box at which point the solution was bright yellow with a yellow ppt. The yellow solid was collected by filtration and then redissolved into methylene chloride, filtered and evaporated to dryness in vacuo. The collected yellow solid was blue-green photoluminescent and soluble in toluene. Material is purified for device work via high vacuum sublimation

Example 4

Zirconium complex of 5-t-butyl-8-hydroxyquinoline

Example 4a

Preparation of the Quinoline Ligand

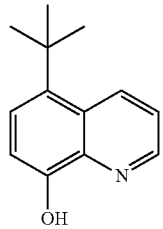

Into a 500 mL 3-neck flask fitted with condenser, addition funnel and a thermometer was added 10.0 g of 2-Amino-4-tert-butylphenol (Aldrich) dissolved in 50.0 mL acetic acid. To the solution was added 3.90 g of 4-(t-butyl)-2-nitrophenol (Aldrich) and 100 mL of concentrated HCl. The contents of the flask were heated to 80° C. by means of an oil bath. Acrolein (Aldrich) (6.78 g) was added over 30 min via the addition funnel. After the addition was complete, the solution was heated to 130° C. for 16 hrs. The solution was allowed to cool to room temperature and then poured into 300 mL cold water and neutralized to pH 7.0 by addition of a 25% NaOH solution. A tan precipitate formed which was extracted from the aqueous solution (3×200 ml methylene chloride). The combined extracts were dried with $MgSO_4$ and concentrated to an oil. The oil was resuspended in methylene chloride and the insoluble materials (unreacted 2-amino-4-tert-butylphenol) filtered off. The filtrate was concentrated to an oil and purified by chromatography on silica gel column eluting with 1:1 chloroform:hexanes to remove the non-polar impurities followed by chloroform to elute the product. The product containing fractions were combined and concentrated to an oil which solidified upon standing. Yield 1.56 g (13%)

Example 4b

Preparation of the Zirconium Complex of Ligand Prepared in 4a

In a glove box, tetrachlorozirconium 0.23 g was dissolved in 10 mL methanol and added to 0.81 g 5-t-butyl-8-hydroxyquinoline (prepared in example 4a above) also dissolved in 10 mL methanol with stirring. The solution immediately turned orange red and gets warm. 0.45 g triethylamine was added dropwise and the solution became hot with a yellow ppt. The mixture was stirred at room temperature for 15 mins in the glove box. The solution remained dirty yellow and then began to precipitate a bright yellow crystalline solid. A yellow solid was collected by filtration, washed with methanol and ~0.8 g product was recovered as a bright yellow microcrystalline solid. The recovered solid was green luminescent and dissolved well in methylene chloride. Material is purified for device work via high vacuum sublimation.

Example 5

Zirconium complex of 5-trifluoromethyl-8-hydroxyquinoline

Example 5a

Preparation of the Quinoline Ligand

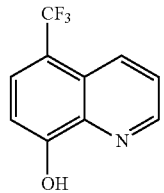

Into a 500 ml RB flask fitted with a reflux condenser, dropping funnel and thermometer was added 20.0 g of 2-methoxy-(5-trifluoromethyl) aniline (Aldrich), 11.57 g nitrobenzene sulfonic acid (Aldrich) and 145 mg of iron (II) sulfate. To the mixture was added 100 ml 85% $H_3PO_4$ with stirring and the suspension was heated to 80° C. Acrolein 11.73 g was added to the hot solution via the dropping funnel during 1 h. After the addition was complete the solution was heated at 100° C. for 20 hrs. The reaction mixture was allowed to come to room temperature and then poured into 300 mL water. The resulting mixture was neutralized with 2N $NH_4OH$ to pH 7.0 and extracted with 3×200 ml methylene chloride. The combined extracts were dried with $MgSO_4$, filtered and concentrated to an oil. The oil was re-dissolved in methylene chloride and the insoluble white powder filtered off. The filtrate was concentrated and purified by silica gel column chromatography eluting with 0-3% MeOH/methylene chloride. The product containing fractions were combined and concentrated to give an oil which solidified upon standing. The solid was dissolved in 100 mL 2N HCl and extracted with methylene chloride. The aqueous solution was made basic with 4N NaOH, extracted with methylene chloride, and dried with $MgSO_4$. Filtration of the salts followed by removal of solvent gave a pale yellow oil (5-trifluoromethyl-8-methoxyquinoline), which solidified upon standing. Yield=8.50 g (36%)

The 5-trifluoromethyl-8-methoxyquinoline 8.50 g was dissolved in 100 mL glacial acetic acid and added to 20 ml HBr in a 100 mL flask. The solution was heated to reflux for 20 hrs. The reaction mixture was allowed to come to room temperature. The reaction mixture was concentrated by removal of 55 mL of solvent under vacuum. The solution was then poured into 100 mL cold water and neutralized with 2N NaOH to pH 7.0. The resulting solution was extracted with 2×100 ml ether, dried with $NaSO_4$, filtered and concentrated to an oil, which solidified upon standing (5.0 g). The crude material was purified by filtration through a short silica gel column where the silica was first washed with 2% TEA in methylene chloride. The column was then dried under $N_2$ pressure and re-solvated with neat methylene chloride. Elution with 2% EtOH/methylene chloride gave 1.41 g of the desired product as a white crystalline solid.

Example 5b

Preparation of Zirconium Complex of Ligand Prepared in 5a

In a glove box, tetrachlorozirconium 0.23 g was dissolved in 10 mL methanol and added to 0.86 g 5-trifluoromethyl-8-hydroxyquinoline also dissolved in 10 mL methanol with stirring. The solution immediately turns orange red and gets warm. 0.45 g triethylamine was added dropwise and the solution gets hot with a slight yellow ppt. This mixture was then stirred at room temperature for 15 mins in the glove box. The solution remains dirty yellow and then slowly begins to precipitate a pale yellow crystalline solid. The yellow solid was then collected by filtration, redissolved into methylene chloride, filtered and evaporated to dryness in vacuum. The resultant yellow solid was green photoluminescent. Material was purified by sublimation prior to device work.

Example 6

Zirconium complex of 5-diphenylamino-8-hydroxyquinoline

Example 6a

Preparation of the Quinoline Ligand

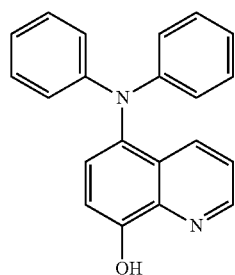

8.98 g, 0.05 mol of 5-chloro-8-hydroxyquinoline (Aldrich), 10.15 g, 0.06 mol of diphenylamine, 350 mL of 1:1 dioxane/toluene, 0.917 g, 0.001 mol $Pd_2DBA_3$, 0.4350 g, 0.0021 mol of tri-t-butylphosphine, and 18.42 g, 0.11 mol lithium bis(trimethylsilyl)amide were combined and refluxed together for a total of 180 hrs. The mixture was cooled to room temperature and filtered through celite with dichloromethane rinses. The mixture was partially evaporated and the organic layer was washed with 1N HCl then neutralized to pH 8 with saturated sodium bicarbonate. The organic layer was then dried with $Na_2SO_4$, filtered and concentrated by rotary evaporation. The product was purified by silica column chromatography using dichloromethane eluent. Yield 11.13 g of a bright yellow solid.

Example 6b

Preparation of the Zirconium Complex of Ligand Prepared in 6a

In a glove box, tetrachlorozirconium 0.23 g was dissolved in 10 mL methanol and added to 1.3 g 5-diphenylamino-8-hydroxyquinoline (prepared in 6a above also dissolved in 10 mL methanol with stirring. The solution immediately turned orange red and became warm. 0.45 g triethylamine was added dropwise and the solution became hot with a yellow-orange ppt. The mixture was stirred and heated to reflux in the glove box for 15 mins. The solution remained bright orange with a dense yellow orange ppt. The orange solid was collected by filtration and then redissolved into methylene chloride, filtered and evaporated to dryness. The resulting red-orange solid was red luminescent. The product was recrystallized from methylene chloride/methanol which originally precipitates as a red oil but which crystallizes to nice clear large orange crystals overnight. The material was sublimed in high vacuum prior to device fabrication Example 7

Zirconium complex of 2-methyl-8-hydroxyquinoline

In a glove box, tetrachlorozirconium 2.33 g was dissolved in 100 mL methanol (gets hot) and added to 6.4 g solid 8-hydroxy-2-methylquinoline also dissolved in 100 mL methanol and the solution becomes yellow with a solid precipitate. Heat to reflux and add toluene and stir. A crusty yellow solid was present at this stage. 4.04 g triethylamine was added dropwise and the solution gets hot with a noticeable dissolution of the yellow precipitate. This mixture was refluxed for 15 mins in the glove box. The solution remained bright yellow and formed a dense pale yellow precipitate. The yellow crystalline solid which was blue green photoluminescent was collected by filtration and washed with methanol and hexanes. The 1-H nmr spectrum in methylene chloride implied a mixture of isomeric materials. The material was sublimed in high vacuum prior to use in devices.

Example 8

Zirconium complex of 7-n-propyl-8-hydroxyquinoline

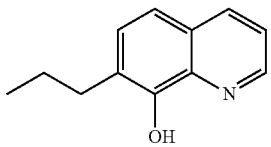

In a glove box, tetrachlorozirconium 0.46 g was dissolved in 10 mL methanol (gets hot) and added to 1.52 g 7-n-propyl-8-hydroxyquinoline (ASDI Inc., 601 Interchange Blvd. Newark, Del., 19711 USA) also dissolved in 10 mL methanol with stirring. The solution immediately turned orange and became warm. 0.9 g triethylamine was added dropwise and the solution became hot with a dense yellow precipitate. This mixture was stirred and refluxed for 15 mins in glove box. The solution remained orange yellow and a precipitate formed as a bright yellow crystalline solid. The yellow solid was filtered off and washed with methanol to recover ~0.8 g product as a bright yellow microcrystalline solid. The product was recrystallized from methylene chloride/methanol resulting in orange yellow crystals.

Example 9

Device Fabrication and Characterization

OLED devices were fabricated by the thermal evaporation technique. The base vacuum for all of the thin film deposition was in the range of $10^{-8}$ torr. Patterned indium tin oxide coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor.

The cleaned, patterned ITO substrate was then loaded into the vacuum chamber and the chamber was pumped down to $10^{-8}$ torr. The substrate was then further cleaned using an oxygen plasma for about 1.5 minutes. After cleaning, multiple layers of thin films were then deposited sequentially onto the substrate by thermal evaporation. Patterned metal electrodes (LiF/Al) were deposited through a mask. The thickness of the films was measured during deposition using a quartz crystal monitor. The completed OLED device was then taken out of the vacuum chamber, encapsulated with a cover glass using epoxy, and characterized.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is cd/A. The power efficiency is the current efficiency divided by the operating voltage. The unit is lm/W.

The materials used in device fabrication are listed below:
DB1: poly(3,4-ethylenedioxythiophene) poly(styrenesulfonate
NPB: N,N'-Bis(naphthalen-1-yl)-N,N'-bis-(phenyl)benzidine
TDATA: 4,4',4"-Tris-(N,N-diphenyl-amino)-triphenylamine
MTDATA: 4,4',4"-Tris(N-3-methylphenyl-N-phenyl-amino)-triphenylamine Red emitter 1:

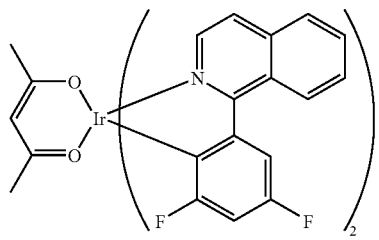

Balq2:

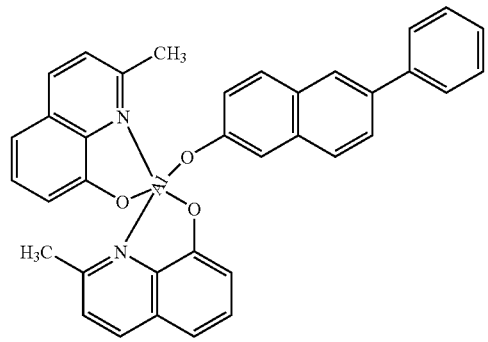

Device configurations (order and identity of layers):

Example A

ITO substrate mTDATA(80 nm)

red emitter 1 (3.2 nm) doped in Balq2 (40 nm)

ETM in example 1(30 nm)

LiF(1 nm)/Al(100 nm).

Example B

ITO substrate

DB1(38 nm)

TDATA(30 nm)

red emitter 1(3.2 nm) doped in Balq2 (40 nm)

Balq2(10 nm)

ETM in Example 2(20 nm)

LiF(1 nm)/Al(100 nm)

Example C

ITO substrate

DB1(46 nm)

TDATA(30 nm)

red emitter 1 (3.2 nm) doped in Balq2 (40 nm)

Balq2(10 nm)

ETM in Example 3(20 nm)

LiF(1 nm)/Al(100 nm)

Example D

ITO substrate

DB1(46 nm)

TDATA(30 nm)

red emitter 1(3.2 nm) doped in Balq2 (40 nm)

Balq2(10 nm)

ETM in Example 4(20 nm)

LiF(1 nm)/Al(100 nm)

Example E

ITO substrate

DB1(45 nm)

TDATA(30 nm)

red emitter 1(3.2 nm) doped in Balq2 (40 nm)

ETM in example 5(30 nm)

LiF(1 nm)/Al(100 nm)

Example F

ITO substrate

DB1(37 nm)

TDATA(30 nm)

red emitter 1 (3.2 nm) doped in Balq2 (40 nm)

Balq2(10 nm)

ETM in Example 6(20 nm)

LiF(1 nm)/Al(100 nm)

Example G

ITO substrate

DB1(46 nm)

NPB(30 nm)

red emitter 1(3.2 nm) doped in Balq2 (40 nm)

ETM in Example 7(30 nm)

LiF(1 nm)/Al(100 nm)

Example H

ITO substrate

DB1(42 nm)

TDATA(30 nm)

red emitter 1(3.2 nm) doped in Balq2 (40 nm)

ETM in Example 8(30 nm)

LiF(1 nm)/Al(100 nm)

TABLE I

Device characterization data

| | Peak current efficiency (cd/A) | Current efficiency (cd/A) at 500 cd/m$^2$ | Power efficiency (lm/W) at 500 cd/m$^2$ | Color coordinates (x, y) |
|---|---|---|---|---|
| Example A | 0.3 | — | — | (0.64, 0.356) |
| Example B | 11 | 5.8 | 1.9 | (0.653, 0.346) |
| Example C | 4.5 | — | — | (0.64, 0.357) |
| Example D | 5.5 | 3.9 | 0.9 | (0.65, 0.35) |
| Example E | 2.2 | 1.4 | 0.3 | (0.64, 0.355) |
| Example F | 8 | 4.2 | 1.1 | (0.65, 0.35) |
| Example G | 0.65 | 0.6 | 0.14 | (0.63, 0.36) |
| Example H | 4.7 | 3 | 0.65 | (0.65, 0.35) |

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An organic electronic device comprising at least one layer comprising at least one complex of the formula:

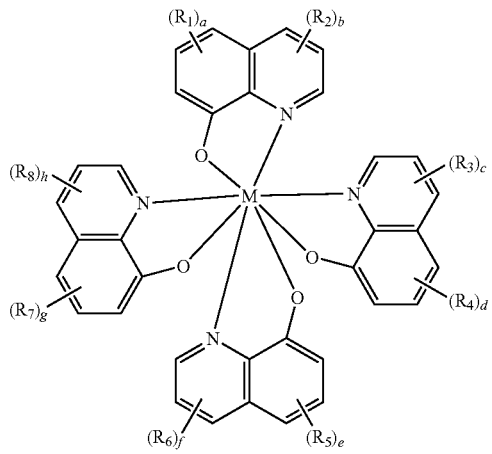

wherein:
M is selected from Ti or Zr,
$R^1, R^2, R^3, R^4, R^5, R^6, R^7$, and $R^8$ are each independently F, Cl, $CF_3$, diarylamine, carbazolyl, alkoxy, cyano, alkyl or aryl; and
a, b, c, d, e, f, g, and h are each 0, 1, 2, or 3, provided that at least one of a, b, c, d, e, f, g, and h is other than 0; and wherein at least one of $R^1, R^2, R^3, R^4, R^5, R^6, R^7$, and $R^8$ is carbazolyl.

2. The device of claim 1 wherein the layer is a charge transport layer.

3. The device of claim 2 wherein the layer is an electron transport layer.

4. The device of claim 1, wherein at least one of $R^1, R^2, R^3, R^4, R^5, R^6, R^7$, and $R^8$ are F or $CF_3$.

5. The device of claim 1, wherein M is Zr.

6. The device of claim 1, wherein at least one of the $R^1, R^2, R^3, R^4, R^5, R^6, R^7$, and $R^8$ groups is diphenylamino.

7. The device of claim 1, wherein M is Zr and a, b, c, d, e, f, g, and h are each 0 or 1.

8. An article useful in the manufacture of an organic electronic device comprising an electron transport layer, said layer comprising at least one complex of the formula:

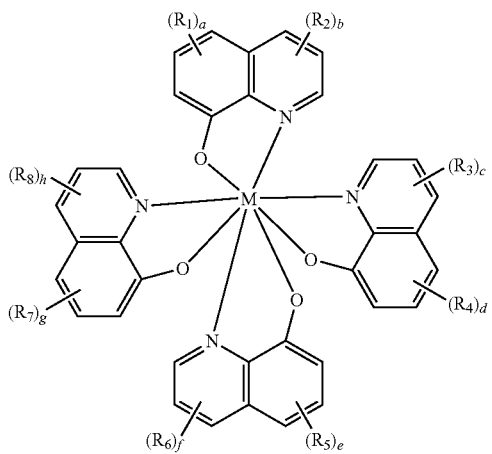

wherein:
M is selected from Ti or Zr,
$R^1, R^2, R^3, R^4, R^5, R^6, R^7$, and $R^8$ are each independently F, Cl, $CF_3$, diarylamine, carbazolyl, alkoxy, cyano, alkyl or aryl; and
a, b, c, d, e, f, g, and h are each 0, 1, 2, or 3, provided that at least one of a, b, c, d, e, f, g, and h is other than 0; provided that at least one of $R^1, R^2, R^3, R^4, R^5, R^6, R^7$, and $R^8$ is carbazolyl.

9. The article of claim 8, wherein at least one of $R^1, R^2, R^3, R^4, R^5, R^6, R^7$, and $R^8$ are F or $CF_3$.

10. The article of claim 8, wherein M is Zr.

11. The article of claim 8, wherein at least one of the $R^1, R^2, R^3, R^4, R^5, R^6, R^7$, and $R^8$ groups is diphenylamino.

12. The article of claim 8, wherein M is Zr and a, b, c, d, e, f, g, and h are each 0 or 1.

* * * * *